United States Patent [19]

Moretz et al.

[11] Patent Number: 5,392,467
[45] Date of Patent: * Feb. 28, 1995

[54] MOISTURE-MANAGEMENT GARMENT AND SUPPORT POUCH GARMENT

[75] Inventors: Herbert L. Moretz, Davidson, N.C.; Daniel L. Brier, Key Largo, Fla.

[73] Assignee: Intelpro Corporation, Lincolnton, N.C.

[*] Notice: The portion of the term of this patent subsequent to Mar. 8, 2011 has been disclaimed.

[21] Appl. No.: 47,841

[22] Filed: Apr. 15, 1993

Related U.S. Application Data

[63] Continuation-in-part of Ser. No. 23,006, Feb. 26, 1993, Pat. No. 5,249,320, which is a continuation-in-part of Ser. No. 3,263, Jan. 12, 1993, Pat. No. 5,269,720, which is a continuation-in-part of Ser. No. 991,761, Dec. 17, 1992, Pat. No. 5,297,296, which is a continuation-in-part of Ser. No. 945,677, Sep. 16, 1992, Pat. No. 5,291,617, which is a continuation-in-part of Ser. No. 842,224, Feb. 26, 1992, Pat. No. 5,210,882, which is a continuation-in-part of Ser. No. 791,066, Nov. 12, 1991, Pat. No. 5,217,782.

[51] Int. Cl.$^6$ .............................................. A41B 9/00
[52] U.S. Cl. .......................................... 2/400; 2/403; 2/406; 2/238; 2/114; 2/409; 604/393; 604/396
[58] Field of Search ................... 2/400, 403, 405, 406, 2/238, 114, 49.1, 48, 53, 173, DIG. 11, 409; 604/358, 378, 385, 393, 394, 396

[56] References Cited

U.S. PATENT DOCUMENTS

| 3,237,625 | 3/1966 | Johnson . | |
| 3,487,833 | 1/1970 | Senser | 2/405 |
| 3,613,687 | 10/1971 | Kennedy . | |
| 3,706,103 | 12/1972 | Senser . | |
| 3,852,828 | 12/1974 | Silverstein . | |
| 4,067,068 | 1/1978 | Bregstein et al. | 2/406 |
| 4,351,340 | 9/1982 | McLeod | 2/406 |
| 4,880,424 | 11/1989 | Rautenberg . | |
| 4,961,419 | 10/1990 | Tribble et al. . | |
| 5,037,409 | 8/1991 | Cehn et al. . | |
| 5,152,014 | 10/1992 | Marx et al. | 2/409 |
| 5,291,617 | 3/1994 | Moretz et al. | 2/400 |

FOREIGN PATENT DOCUMENTS 327823 8/1989 European Pat. Off. .

OTHER PUBLICATIONS

The Sign of Winners, Published by: Akzo Fibres and polymers division, undated. Hydrofil nylon, by Allied Signal, 1988.
Industrial Fabric Opportunities for Hydrophilic Nylons, by Judy Peters, Gordon and Breach Science Publishers, from Polymer News, 1990, vol. 15, pp. 238–244.

Primary Examiner—Andrew M. Falik
Assistant Examiner—Gloria Hale
Attorney, Agent, or Firm—W. Thad Adams, III

[57] ABSTRACT

A moisture-management garment and support garment including a moisture-management panel which extends from an upper crotch area of the garment to a lower crotch area of the garment. The panel includes an inner fabric layer, intermediate fabric layer, and an outer fabric layer. The inner fabric layer is constructed of wicking yarns for residing in skin contact during garment wear. The intermediate fabric layer comprises one or more moisture transport inserts which reside adjacent to the inner fabric layer for transporting moisture away from the inner fabric layer and away from the skin of the wearer. An outer fabric layer resides adjacent the intermediate fabric layer for receiving and dispersing moisture wicked outwardly from the inner and intermediate fabric layers.

31 Claims, 6 Drawing Sheets

MOISTURE-MANAGEMENT GARMENT AND SUPPORT POUCH GARMENT

This application is a continuation-in-part of application Ser. No. 023,006, filed on Feb. 26, 1993, now Pat. No. 5,249,320, which is a continuation-in-part of application Ser. No. 003,263, filed on Jan. 12, 1993, now Pat. No. 5,269,720, which is a continuation-in-part of application Ser. No. 991,761, now Pat. No. 5,297,296, filed on Dec. 17, 1992, which is a continuation-in-part of application Ser. No. 945,677, now Pat. No. 5,291,617, filed Mar. 8, 1994, filed on Sep. 16, 1992, which is a continuation-in-part of application Ser. No. 842,224, now Pat. No. 5,210,882, filed on Feb. 26, 1992, which is a continuation-in-part of application Ser. No. 791,066, now Pat. No. 5,217,782, filed on Nov. 12, 1991.

TECHNICAL FIELD AND BACKGROUND OF THE INVENTION

This invention relates to garments, particularly undergarments and panty hose for normal, regular and everyday use having a crotch area constructed from a moisture-management fabric. The invention also relates to support undergarments, such as athletic supporters, for particular use during recreation and exercise.

The fabric composite from which these garments, or portions thereof, are constructed is intended to quickly move moisture away from the skin of the wearer, while enhancing the dispersion of the moisture to those fibers of the fabric which do not touch the skin, and facilitating its evaporation through the outer shell. One such fabric is the "Coolmax" or "Thermax" fabric manufactured by DuPont. This fabric, when incorporated in the present invention, is particularly effective for wicking moisture away from the skin of the wearer, and not adding noticeable bulk to the crotch area of the garment.

Typical moisture-management garments include several layers of moisture absorbing material and a moisture barrier material to prevent leakage through the garment onto outer clothing. These type undergarments are expensive, bulky, and generally quite uncomfortable. Moreover, these undergarments usually include a continuous front panel constructed entirely of moisture-absorbing fabric layers, having no fly opening.

The present invention eliminates this problem by providing an undergarment with a fly opening that does not compromise the undergarment's ability to effectively absorb and disperse moisture to drier areas of the garment for evaporation. The particular fly opening satisfies the long felt need for a garment possessing all the features of a normal undergarment with the addition of moisture-management characteristics. Moreover, the crotch area of the present invention retains the feel and appearance of a regular brief, but with superior features for managing perspiration.

The invention also relates to a woman's panty and panty hose. The effective management of moisture in such garments has been a problem. Prior art undergarments do not adequately address this problem. Generally, these garments include a cotton crotch panel which holds moisture within the fibers next to the skin creating an environment conducive to bacteria, fungus, and yeast growth. The present invention provides an undergarment or a panty hose garment for a woman with effective moisture managing features, while maintaining the general characteristics and appearance of a conventional undergarment.

The support undergarment of the present invention satisfies the need for effective moisture-management in a comfortable athletic support undergarment for men. The moisture managing characteristics of this garment help prevent chafing, irritation and conditions conducive to bacteria and fungus growth.

SUMMARY OF THE INVENTION

Therefore, it is an object of the invention to provide a moisture-management garment which includes portions, such as crotch portions, constructed from a fabric having moisture-management characteristics.

It is another object of the invention to provide a moisture-management garment which comprises a woman's panty hose with the outer shell fabric of the crotch area constructed of a hydrophilic material, such as hydrophilic nylon.

It is another object of the invention to provide an ordinary underwear garment having moisture-management characteristics, but which does not include a moisture barrier element.

It is another object of the invention to provide a moisture-management garment designed for general wear, without noticeable bulk.

It is another object of the invention to provide a moisture-management garment which includes a top panel located in the front waist portion of the garment and a moisture-management panel located below the top panel.

It is another object of the invention to provide a moisture-management garment which includes an overlapping fly opening formed between the top panel and the moisture-management panel.

It is another object of the invention to provide a moisture-management garment including a moisture-management panel which can be incorporated into the crotch area of garments, such as women's panties, panty hose, men's boxers and briefs, pajamas, athletic apparel and the like.

It is another object of the invention to provide a moisture-management garment Which includes a moisture-management panel constructed of fibers designed to wick and transport moisture from a lower area of the garment crotch where moisture tends to accumulate to a drier area of the garment.

It is another object to provide a moisture-management garment including a moisture-management panel which demonstrates a positive wicking action to pull moisture against the pull of gravity upwardly away from the crotch and towards the waist of the garment where the moisture can more easily be dispersed.

It is another object of the invention to provide a moisture-management garment including a moisture-management panel which promotes quick evaporation of moisture while retaining stretch for comfort.

It is another object of the invention to provide a moisture-management garment which is a support garment for particular use during periods of recreation and high activity, and for providing added support to the crotch area of the garment.

It is another object of the invention to provide a moisture-management support garment which comprises an athletic supporter.

It is another object of the invention to provide a moisture-management support garment which comprises a man's brief.

It is another object of the invention to provide a moisture-management support garment which includes a moisture-management pouch constructed from a fabric composite having moisture-management characteristics.

It is another object of the invention to provide a moisture-management support garment which includes a moisture-management pouch constructed of fibers designed to wick and transport moisture from a lower area of the garment crotch where moisture tends to accumulate to a drier area of the support garment.

It is another object of the invention to provide a moisture-management support garment including a moisture-management pouch which demonstrates a positive wicking action to pull moisture against the pull of gravity upwardly away from the crotch and towards the waist of the garment where the moisture can more easily be dispersed.

It is another object of the invention to provide a moisture-management support garment including a moisture-management pouch which promotes quick evaporation of moisture.

It is another object of the invention to provide a moisture-management support garment which includes a relatively wide waistband for holding the support garment and support pouch close to the body of the wearer.

These and other objects of the present invention are achieved in the preferred embodiments disclosed below by providing an improved moisture-management garment constructed of an outer shell fabric, and including a moisture-management panel which extends from an upper crotch area of the garment to a lower crotch area of the garment. The panel includes an inner fabric layer, intermediate moisture transport inserts, and an outer fabric layer. The inner fabric layer is constructed of moisture wicking fibers for residing in skin contact during garment wear. One or more intermediate moisture transport inserts reside adjacent to the inner fabric layer for transporting moisture away from the inner fabric layer and away from the skin of the wearer. An outer fabric layer resides adjacent the intermediate fabric layer for receiving and dispersing moisture wicked outwardly from the inner and intermediate fabric layers. The outer fabric layer comprises the outer shell fabric of the panel.

According to another preferred embodiment of the invention, the garment further includes a top panel. The top panel extends from a front waist portion of the garment to the upper crotch area of the garment, partially overlapping the moisture-management panel. The top panel and the moisture-management panel define a laterally-extending fly opening formed therebetween.

According to one preferred embodiment of the invention, the inner fabric layer is constructed of hydrophobic yarns.

According to yet another preferred embodiment of the invention, the inner fabric layer is constructed of yarns chosen from the fiber group consisting of polyester, polypropylene, and nylon.

Preferably, the inner fabric layer includes fibers having a high surface area in relation to volume.

According to one preferred embodiment of the invention, the moisture transport insert is constructed of hydrophobic yarns.

According to another preferred embodiment of the invention, the moisture transport insert is constructed of yarns chosen from the fiber group consisting of polyester, cotton, rayon, nylon, polypropylene, and a blend of polyester and cotton.

According to another preferred embodiment of the invention, the moisture transport insert defines a fabric panel, the width of which tapers from the upper crotch area towards the lower crotch area of the garment. The moisture transport insert provides greater surface area and moisture absorption capacity in the upper crotch area to promote transport of moisture upwardly towards a drier area of the garment.

Preferably, the moisture transport insert is secured to at least one of the inner and outer fabric layers by sewing stitches.

According to one preferred embodiment of the invention, the outer fabric layer is constructed of hydrophilic yarns.

According to another preferred embodiment of the invention, the outer fabric layer is constructed of yarns chosen from the fiber group consisting of hydrophilic nylon, cotton, a blend of cotton and polyester, rayon, and a blend of hydrophilic nylon and conventional nylon.

According to one preferred embodiment of the invention, the garment comprises a man's brief.

According to another preferred embodiment of the invention, the garment comprises a man's boxer short or pajama bottom.

According to yet another preferred embodiment of the invention, the garment comprises a woman's panty.

According to yet another preferred embodiment of the invention, the garment comprises a woman's panty hose.

A moisture-management support garment, according to one preferred embodiment, includes a moisture-management support pouch secured to and extending generally from a front waist area of the garment to a lower crotch area of the garment. The support pouch includes an inner fabric layer, intermediate moisture transport inserts, and an outer fabric layer. The inner fabric layer is constructed of moisture wicking fibers for residing in skin contact during garment wear. One or more intermediate moisture transport inserts reside adjacent to the inner fabric layer for transporting moisture away from the inner fabric layer and away from the skin of the wearer. An outer fabric layer resides adjacent the intermediate fabric layer for receiving and dispersing moisture wicked outwardly from the inner and intermediate fabric layers. The outer fabric layer comprises the outer shell fabric of the support pouch.

According to one preferred embodiment of the invention, the inner fabric layer is constructed of hydrophobic yarns.

According to another preferred embodiment of the invention, the inner fabric layer is constructed of yarns chosen from the fiber group consisting of polyester, polypropylene, and nylon.

Preferably, the inner fabric layer includes fibers having a high surface area in relation to volume.

According to another preferred embodiment of the invention, the inner fabric layer includes elastic fibers for providing added stretch and support strength in the support pouch of the garment.

According to one preferred embodiment of the invention, the one or more moisture transport inserts are constructed of hydrophobic yarns.

According to another preferred embodiment of the invention, the one or more moisture transport inserts are constructed of yarns chosen from the fiber group consisting of rayon, nylon, polypropylene, polyester, cotton, and a blend of polyester and cotton.

According to another preferred embodiment of the invention, the one or more moisture transport inserts include elastic fibers for allowing the moisture transport inserts to stretch as the inner and outer fabric layers stretch.

Preferably, the one or more moisture transport inserts are secured to at least one of the inner and outer fabric layers.

According to yet another preferred embodiment of the invention, the moisture transport inserts comprise first and second longitudinally-extending wicking strips positioned in respective side sections of the moisture-management support pouch. The inserts extend generally from the waist area of the garment to the lower crotch area of the garment.

According to one preferred embodiment of the invention, the outer fabric layer is constructed of hydrophobic yarns.

According to another preferred embodiment of the invention, the outer fabric layer is constructed of hydrophilic yarns.

According to yet another preferred embodiment of the invention, the outer fabric layer is constructed of a blend of hydrophilic and hydrophobic yarns.

According to yet another preferred embodiment of the invention, the outer fabric layer is constructed of yarns chosen from the fiber group consisting of hydrophilic nylon, cotton, a blend of cotton and polyester, rayon, and a blend of hydrophilic nylon and conventional nylon.

Preferably, the outer fabric layer includes elastic fibers for proving added stretch and support strength in the support pouch of the garment.

According to one preferred embodiment of the invention, the support garment further includes a relatively wide waistband for holding the support garment and the moisture-management pouch close to the body of the wearer.

Preferably, the waistband is constructed of elastic yarns and yarns chosen from the fiber group consisting of nylon, cotton, rayon, and blends of hydrophilic nylon and conventional nylon.

According to one preferred embodiment of the invention, the support garment comprises a man's brief.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Moisture-Management Garment

Figure 1:
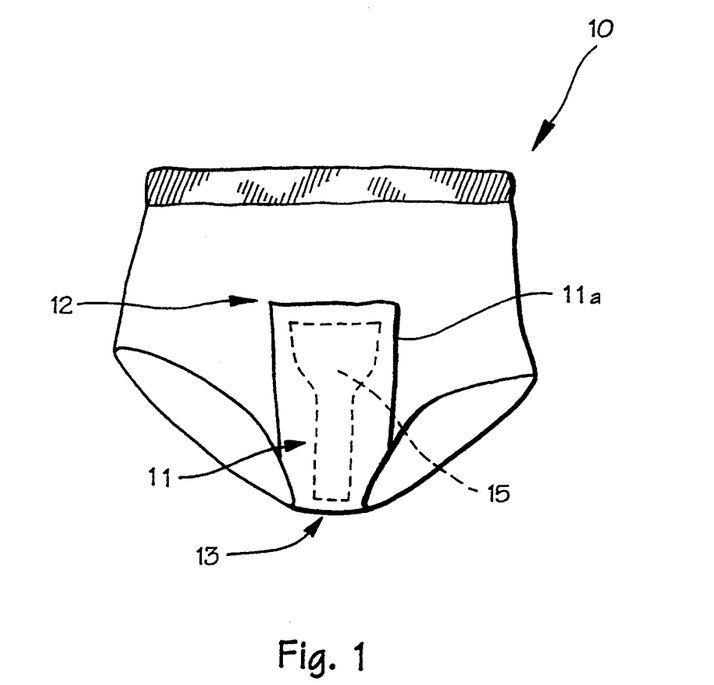
FIG. 1 is a front view of an undergarment with a moisture-management construction according to one embodiment of the present invention.

Referring now specifically to the drawings, a moisture-management garment according to one embodiment of the present invention is illustrated in Figure i and shown generally at reference numeral 10. The garment 10 according to this embodiment is wearable by both men and women. Additionally, several other dress applications, such as pajama bottoms or sports apparel, may be constructed by including the characteristics of the present invention in otherwise conventionally-constructed garments.

Figure 2:
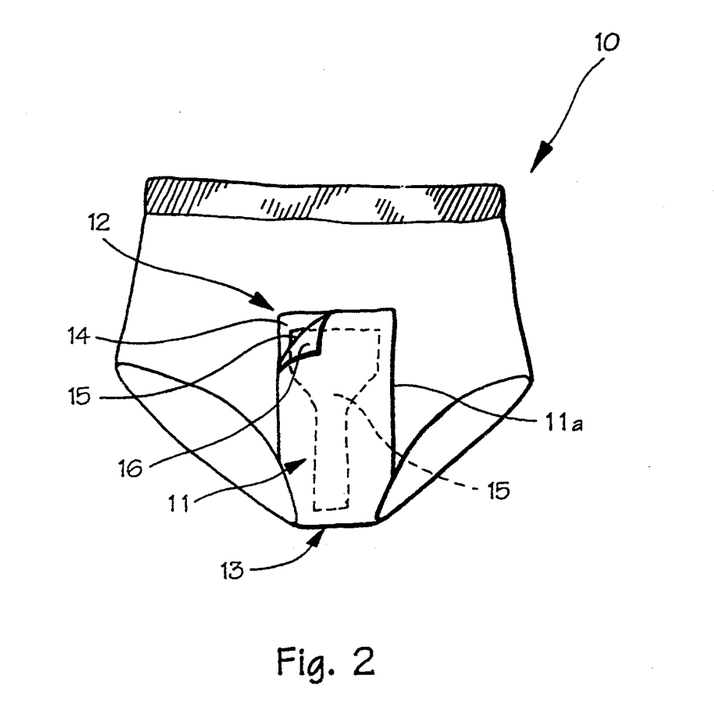
FIG. 2 is a front view of the moisture-management panel with a portion broken away to show the positioning of each of the inner and outer fabric layers, and the intermediate moisture transport insert.

The undergarment 10 is preferably formed of conventional knit fabric, and includes a moisture-management panel 11 which extends generally from an upper crotch area 12 to a lower crotch area 13 of the undergarment 10. Preferably, the moisture-management panel 11 comprises the entire crotch area of the undergarment 10, and is sewn to the .interior surface of the undergarment 10. The stitching 11a is shown in FIGS. 1 and 2. Preferably, the stitching 11a is a close, tight stitch that is relatively invisible. According to another preferred embodiment (not shown), the moisture-management panel 11 extends from the upper crotch area 12, beyond the lower crotch area 13, and upwardly towards the back waistline of the undergarment 10.

The moisture-management panel 11 includes a moisture transport insert 15. Preferably, the moisture transport insert 15 is shaped to taper from top to bottom, or from the upper crotch area 12 to the lower crotch area 13. According to another embodiment (not shown), the moisture transport insert 15 is triangular. The tapering effect provides greater moisture absorption and dispersal in the upper portion of the undergarment 10, where moisture can be carried to drier areas for quicker evaporation. Moreover, the relatively narrow strip of moisture transport insert 15 positioned in the lower crotch area 13 provides less bulk between the legs and greater comfort to the wearer.

FIG. 2 illustrates the assembly of the moisture-management panel 11 with a portion broken away to show the positioning of the various fiber layers. An inner fabric layer 14, which resides in skin contact during garment wear, is constructed of soft, wicking yarns. Preferably, these yarns comprise polyester fibers, such as those manufactured by DuPont under the trademark "Coolmax" or "Thermax." According to another embodiment, other yarns such as polypropylene, nylon, wool, cotton, or rayon may be included in the inner fabric layer 14. Preferably, the inner fabric layer 14 is an open-knit or loose knit material having fibers with longitudinally-extending channels and a high surface area in relation to volume. These such fibers possess an exceptional ability to transport moisture away from the skin of the wearer.

The intermediate moisture transport insert 15 resides adjacent the inner fabric layer 14 for receiving and further transporting moisture away from the inner fabric layer 14 and away from the skin of the wearer. Preferably, the moisture transport insert 15 comprises one layer of hydrophobic fibers. However, according to another preferred embodiment, the moisture transport insert 15 includes a plurality of a knit or woven fabric layers. Additionally, other yarns such as those chosen from the fiber group including rayon, nylon, polypropylene, polyester, cotton, or a blend of polyester and cotton may be used for achieving a similar effect. Preferably, these fibers are chemically treated to enhance their wicking capacity. Once treated, otherwise non-wicking fibers will act to wick or move moisture against the pull of gravity, and ultimately, to drier areas of the garment for evaporation. The Intera Corporation and Millikan Corporation are currently utilizing respective processes for chemically treating such fibers for this purpose.

According to one preferred embodiment, the moisture transport insert 15 is constructed of "Coolmax" or "Thermax" polyester fibers. Although one object of the invention is to provide a general-wear undergarment without a bulky crotch panel, the moisture transport insert 15 may include a plurality of fiber layers (not shown) and still maintain the normal feel and appearance of regular underwear.

The particular tapered shape of the moisture transport insert 15, as discussed above, provides increased surface area of wicking fibers leading upwards towards normally drier areas of the garment 10. This creates a positive wicking action to pull moisture against the pull of gravity away from the crotch and towards the waist of the garment where the moisture can more easily be dispersed.

Preferably, the moisture transport insert 15 is sewn to the surface of the inner fabric layer 14 using conventional stitching techniques.

An outer fabric layer 16 is positioned adjacent the moisture transport insert 15, and according to one embodiment is partially adjacent the inner fabric layer 14. Preferably, the outer fabric layer 16 is constructed of fibers, such as hydrophilic nylon, cotton, cotton/polyester blends, rayon, and blends of hydrophilic nylon and conventional nylon. Other such hydrophilic fibers may also be used. The outer fabric layer 16 comprises the outer shell fabric of the moisture-management panel 11. The outer fabric layer 16, or the shell fabric, is conventionally constructed of combed cotton or cotton/polyester knitted fabric.

According to one preferred embodiment, the inner fabric layer 14 is attached to the outer fabric layer 16 along the perimeter of the moisture-management panel 11. The moisture transport insert 15 may also be attached in this manner. However, it is preferred that the moisture transport insert 15 be attached to the outer surface of the inner fabric layer 14, as discussed above.

The moisture transport insert 15 may alternatively be attached to the underside of the outer fabric layer 16. The means for attaching the fabric layers may be any conventional stitch technique known in the art.

Figures 3, 4:
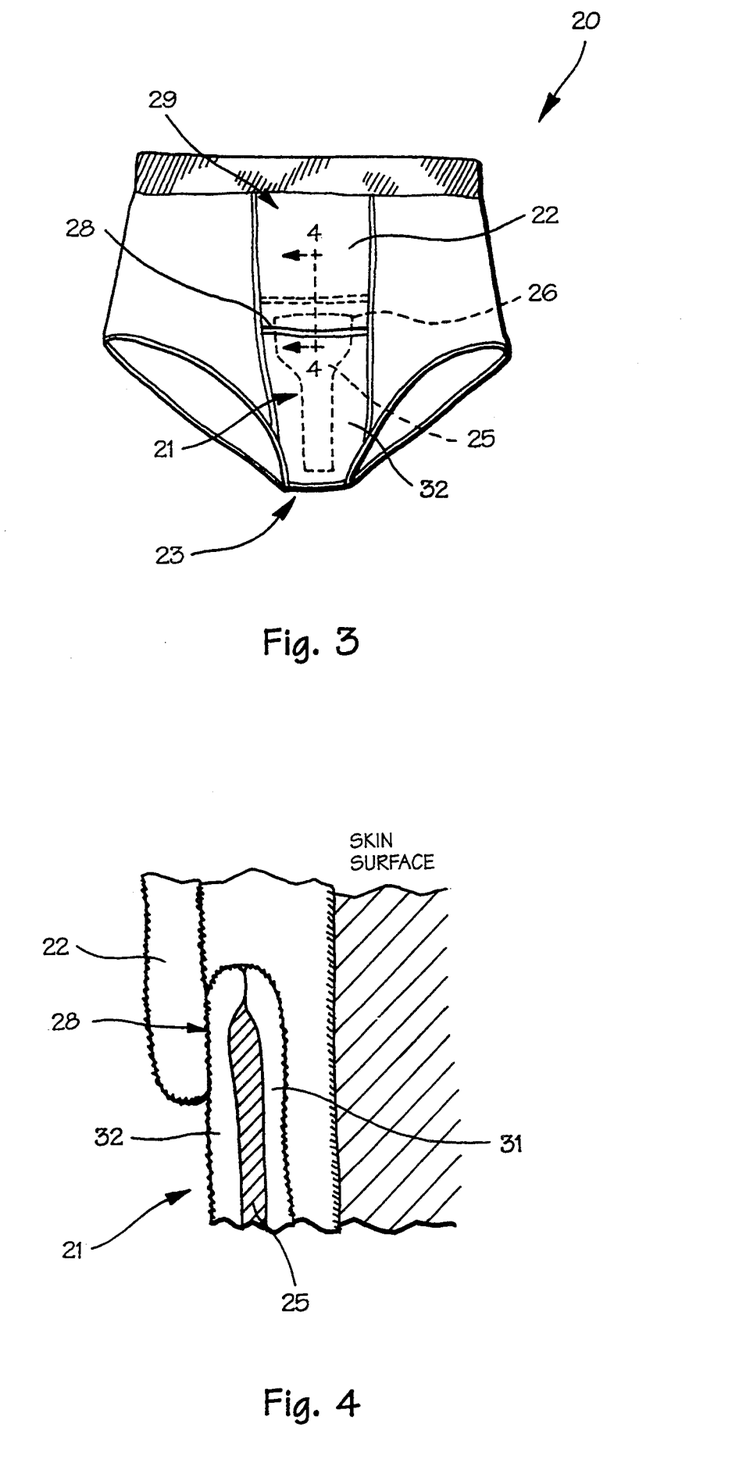
FIG. 3 is a front view of a male undergarment with a moisture-management construction and a fly opening according to another embodiment of the invention.
FIG. 4 is a cross-sectional view of the overlapping top panel and moisture-management panel of the undergarment shown in FIG. 3, taken along lines 4—4 of FIG. 3.

Referring now to FIGS. 3 and 4, a second embodiment of a moisture-management undergarment 20 particularly for men is illustrated. According to this embodiment, the undergarment 20 includes inner and outer knitted fabric layers 31 and 32, and a moisture transport insert 25. It is noted that the fabric construction and assembly of the fabric layers 31 and 33, and the moisture transport insert 25, is identical to that described in reference to the embodiment of undergarment 10 shown in FIGS. 1 and 2.

In addition to the features shown and described in reference to undergarment 10, undergarment 20 further includes a laterally-extending fly opening 28. The fly opening 28 is located between a top panel 22 and the moisture-management panel 21 of the undergarment 20. According to this embodiment, the undergarment 20 can be used for general wear, like a regular undergarment for men, and is especially suited for individuals who perspire heavily or those with occasional mild incontinence.

Preferably, the top panel 22 extends from the front waist portion 29 of the undergarment 20 to just below the top section 26 of the moisture-management panel 21 such that the top panel 22 partially overlaps the moisture-management panel 21 approximately 1 to 3 inches. This overlap provides an unbroken area for wicking and evaporation, as shown in FIG. 4. Additionally, the overlap provides a double layer of shell fabric in the area where the moisture transport insert 25 is widest (See FIG. 3). The openable fly and overlap feature facilitate the management of moisture, either from perspiration in the waist area or from perspiration or other moisture wicked upward from the crotch area. According to another embodiment (not shown), the top panel 22 extends from the entire waist area of the undergarment 20 and overlaps just below the moisture-management panel 21, as discussed above.

Figure 5:
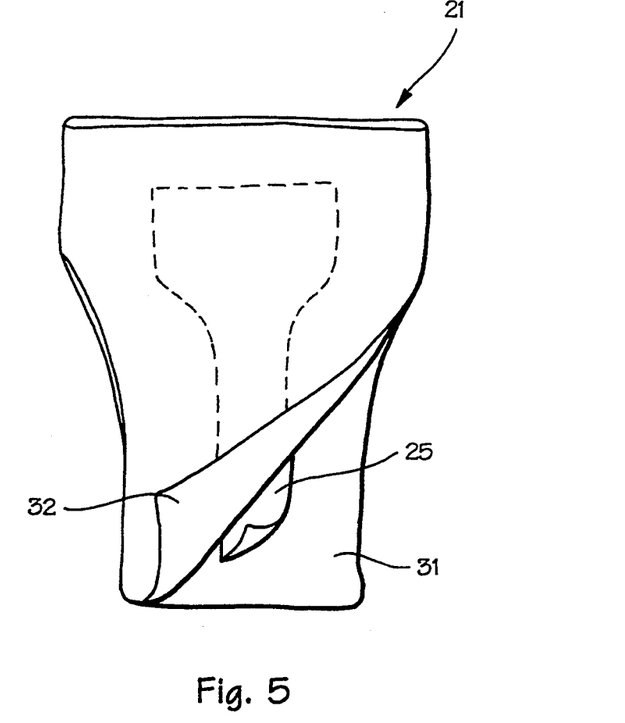
FIG. 5 is a plan view of a moisture-management panel with elements broken away to show assembly details.

The moisture-management panel 21 and moisture transport insert 25 are shown in detail in FIG. 5. Although reference is made particularly to one embodiment of the undergarment 20, the features of these two elements are identical for either of the above-described embodiments of undergarments 10 and 20. Assembly of the moisture-management panel 21 is also illustrated in FIG. 5. As shown, the moisture transport insert 25 is preferably narrower at the lower crotch area 23 for added comfort to the wearer. According to one embodiment, the width of the insert 25 at this point is approximately 0.5 to 1.5 inches. As the insert 25 extends toward the upper crotch area 24, it widens to provide a relatively large surface area of wicking material. At the widest point, the width of the insert 25 is approximately 2 to 4 inches. Preferably, the width of the insert 25 at the lower crotch area 23 remains relatively constant before widening to provide maximum comfort between the legs of the wearer, while maintaining the moisture-management characteristics of the undergarment.

Figure 6:
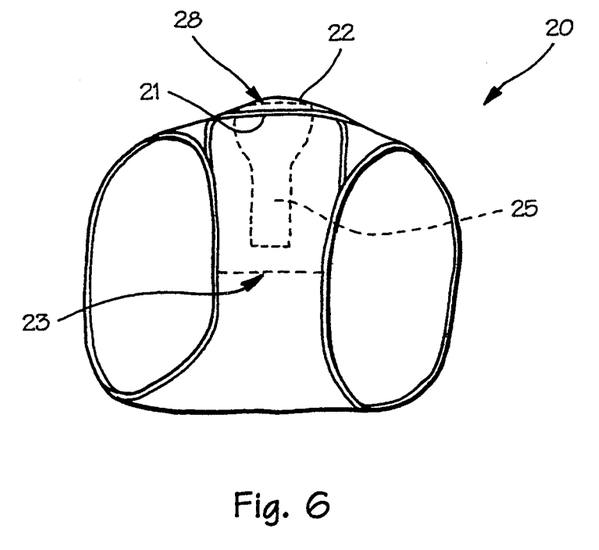
FIG. 6 is a bottom view, looking upwardly, of the moisture-management undergarment of the present invention.

FIG. 6 is a bottom view, looking upwardly, of the undergarment 20. This view best illustrates the location of the moisture-management panel 21 and moisture transport insert 25 in the lower crotch area 23 of the undergarment. It is noted that this view also illustrates the identical positioning of the corresponding moisture-management panel 11 and moisture transport insert 15 of the undergarment 10.

Figure 7:
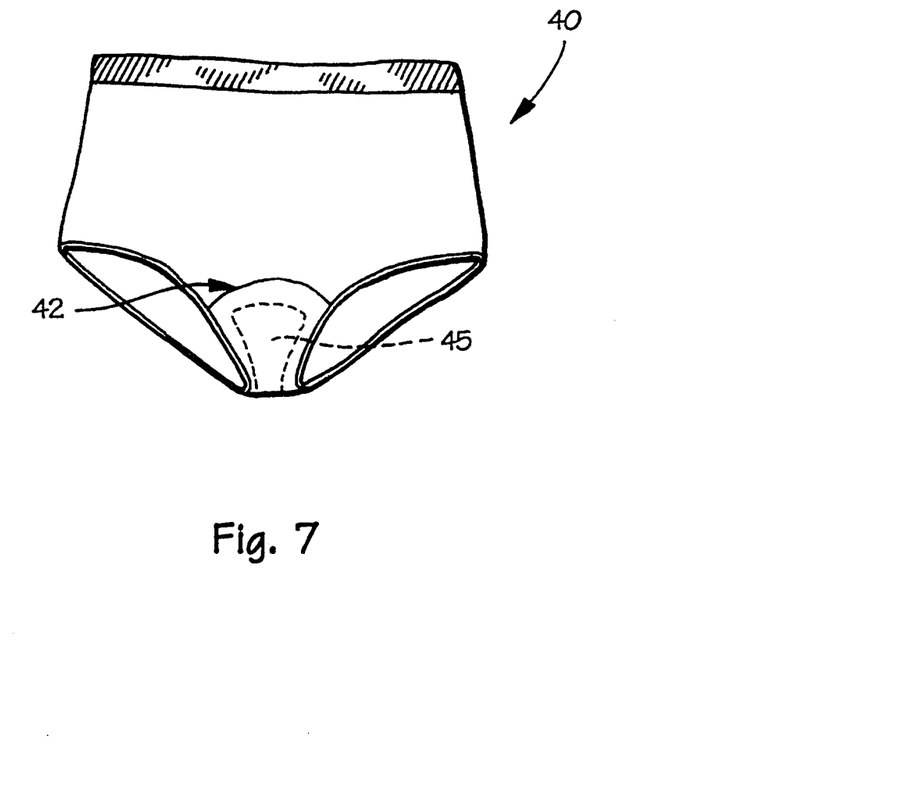
FIG. 7 is a front view of an undergarment according to one preferred embodiment of the invention, particularly suited for women.
Figure 8:
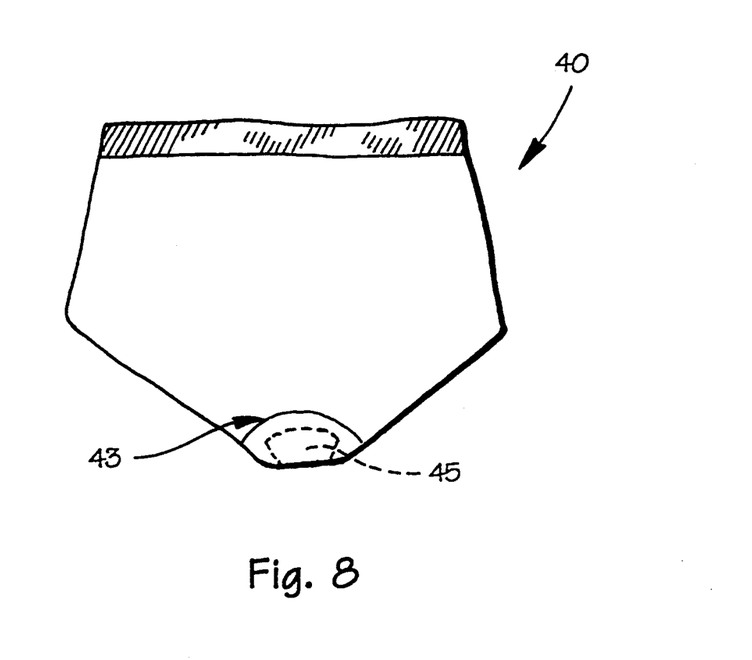
FIG. 8 is a back view of the undergarment shown in FIG. 7.

FIGS. 7 and 8 are respective front and back views of an undergarment 40 particularly suited for women. According to this embodiment, the moisture transport insert 45 is preferably shaped generally in the form of an hourglass to provide greater wicking action in the upper and lower areas of the crotch, 42 and 43. The moisture transport insert 45 may be formed in any number of different shapes to accommodate the particular needs of the wearer.

Figure 9:
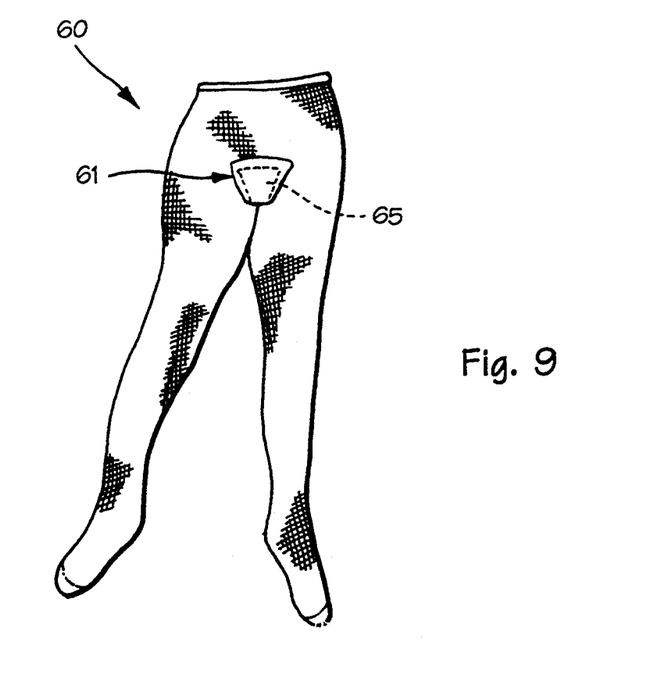
FIG. 9 is a front view of a woman's panty hose according to another preferred embodiment of the invention.

FIG. 9 illustrates an application of the present invention in a pair of women's panty hose 60. Again, according to this embodiment, the shape of the moisture transport insert 65 and moisture-management panel 61 can vary depending upon the specific needs of the wearer. According to one embodiment (not shown), the moisture-management panel 61 extends upwardly, beyond the upper crotch area and towards the waistline of the garment. The panel 61 may also extend around the lower crotch area and towards the back seat area of the garment. Preferably, the outer fabric layer 62 of the moisture-management panel 61 in panty hose 60 is constructed of hydrophilic yarns, such as hydrophilic nylon or cotton. According to another embodiment, the outer fabric layer 62 of the moisture-management panel 61 is constructed of a conventional nylon, or other similar hydrophobic material.

Moisture-Management Support Garment

Figure 10:
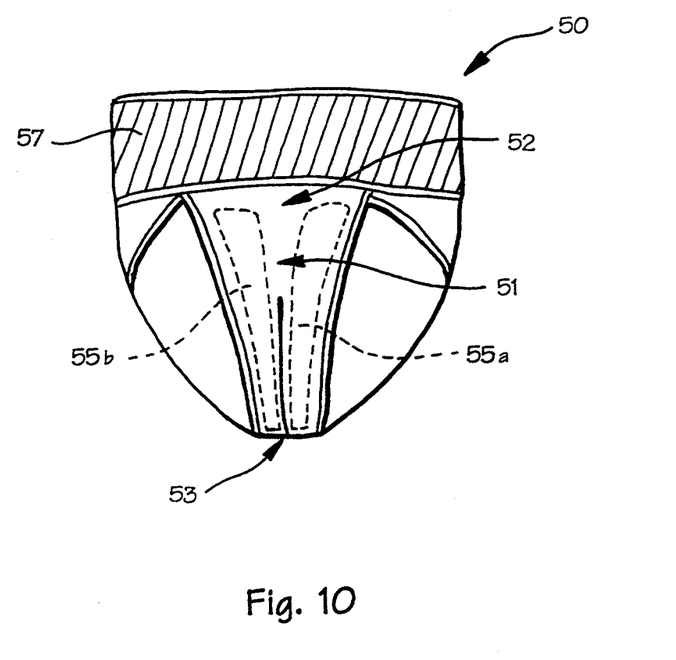
FIG. 10 is a front view of a male support undergarment according to one embodiment of the invention.

A moisture-management support garment according to one embodiment of the present invention is illustrated in FIG. 10, and shown generally at reference numeral 50. The support garment 50 includes a support pouch 51 constructed of moisture-management fabric layers, preferably of conventional knitted construction, for wicking moisture away from the skin and transporting it to drier areas for evaporation. Although FIG. 10 illustrates the support pouch 51 in a men's brief style, the pouch 51 is equally suitable for conventional type athletic supporters, or "jock straps."

Figure 11:
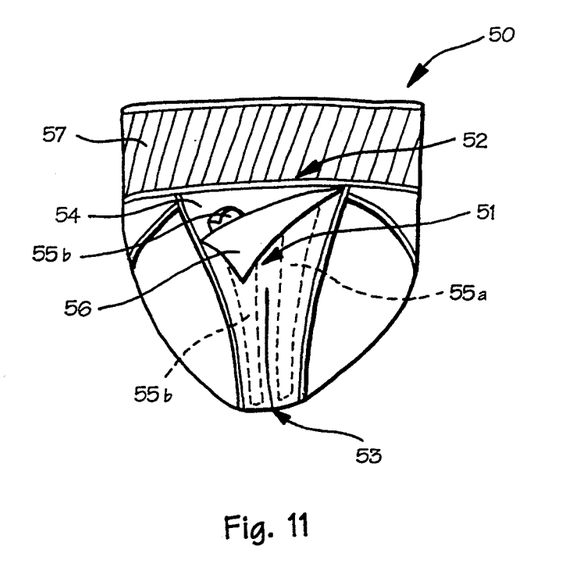
FIG. 11 is a front view of the support undergarment shown in FIG. 10 with elements broken away to illustrate assembly details.

As shown in FIGS. 10 and 11, the pouch 51 includes inner and outer fabric layers 54 and 56, and a pair of intermediate moisture transport inserts 55a and 55b. The inner fabric layer 54, which resides next to the skin of the wearer, is constructed of wicking fibers and elastic fibers, such as spandex or other elastomeric polymers. According to one preferred embodiment, the wicking fibers comprise the hydrophobic polyester fibers manufactured by DuPont under the trademark "Coolmax" or "Thermax." These type fibers are soft and comfortable against the skin. The "Coolmax" polyester fibers also have a high surface area in relation to volume, with longitudinal channels for wicking moisture. Other fibers including polypropylene, nylon, cotton, wool, rayon, or any desired blends of these fibers may also be included to attain a moisture-management effect. The elastic fibers add stretch and added support strength to the support garment 50.

Intermediate moisture transport inserts 55a and 55b are also constructed of wicking fibers and elastic fibers, such as spandex. The fibers used in the moisture transport inserts may include those chosen from the fiber group including polyester, cotton, rayon, nylon, polypropylene, or a blend of polyester and cotton. Preferably, the inserts 55a and 55b are sewn to the inner surface of the outer fabric layer 56, leaving a smooth surface on the inner fabric layer 54 next to the skin. According to one embodiment, the moisture transport inserts 55a–b comprise wicking strips. According to another embodiment (not shown), the pouch 51 includes only one moisture transport insert 55.

Figure 12:
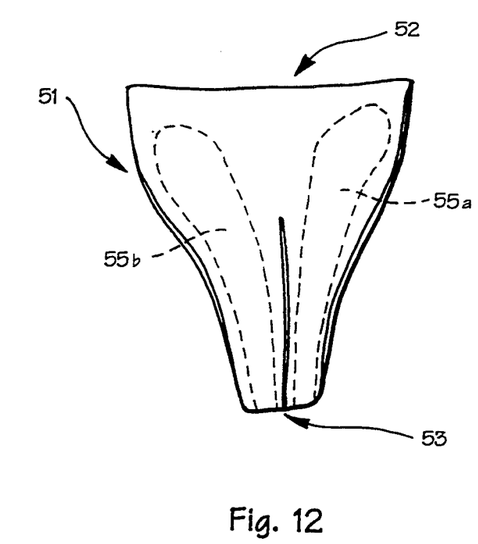
FIG. 12 is a plan view of the moisture-management support pouch of the support undergarment shown in FIG. 10.

FIG. 12 best illustrates the positioning of the moisture transport inserts 55a and 55b. According to one preferred embodiment, the positioning of inserts 55a–b is designed to provide added support along the sides of the pouch 51 where the male genitalia normally reside. The inserts 55a–b also, provide added protection in this rather sensitive area. According to another embodiment, the moisture transport inserts 55a–b include a plurality of knit or woven fabric layers. Additionally, the inserts 55a–b provide extra wicking fibers to wick moisture upwardly from the relatively narrow lower crotch area 53 of the pouch 51 to the wider front waist area 52 of the pouch 51. Since the front waist area 52 is typically drier, moisture is more effectively dispersed and more readily evaporated.

The outer fabric layer 56 of the pouch 51 is constructed of fibers which absorb and disperse moisture wicked outwardly from the inner fabric layer 54 and intermediate moisture transport inserts 55a–b. Preferably, the outer fabric layer 56 comprises the outer shell material of the support pouch 51. Elastic fibers, like spandex, are also included in the outer fabric layer 56 for providing added support, and to allow the outer shell material to stretch as the inner fabric layer 54 and moisture transport inserts 55a–b stretch. According to one embodiment of the invention, the outer fabric layer 56 is comprised either of hydrophobic, hydrophilic, or a blend of hydrophilic and hydrophobic fibers. Preferably, such fibers are chosen from the fiber group consisting of hydrophilic nylon, cotton, cotton/polyester blends, rayon, and blends of hydrophilic nylon and conventional nylon. According to another embodiment, such fibers include polyester, cotton, or a blend of polyester and cotton.

The waistband 57 of the support garment 50 includes rubber or elastic yarns, and is preferably wider than that of a conventional undergarment. According to one embodiment, the waistband 57 is approximately 1 to 3 inches wide. The elastic yarns, or spandex, provides sufficient elasticity to hold support pouch 51 and support garment 50 closely against the body of the wearer. This feature increases the level of comfort, and reduces the risk of injury to the wearer during active periods of recreation.

Figure 13:
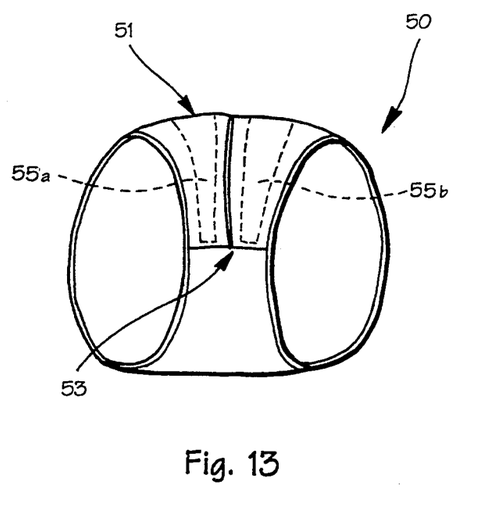
FIG. 13 is a bottom view, looking upwardly, of the undergarment shown in FIG. 10.

FIG. 13 shows a bottom view of the support garment 50. The lower crotch area 53 of the support pouch 51 is best represented in this view.

Preferably, the fabrics of the support garment 50 are treated with an anti-bacterial agent to retard odor and prevent bacteria growth. This treatment is also equally appropriate for the moisture-management undergarments 10, 20 and 60.

A moisture-management garment and support garment according to the present invention are described above. Various details of the invention may be changed without departing from its scope. Furthermore, the foregoing description of the preferred embodiment of the invention is provided for the purpose of illustration only and not for the purpose of limitation—the invention being defined by the claims.

I claim:

1. In a moisture-management garment constructed of an outer shell fabric, the improvement comprising a moisture-management panel extending generally from an upper crotch area of said garment to a lower crotch area of said garment, said panel comprising:
   (a) an inner fabric layer including moisture wicking fibers for residing in skin contact during garment wear;
   (b) an intermediate fabric layer comprising a moisture transport insert residing adjacent to said inner fabric layer, said moisture transport insert formed of one or more fabrics for receiving moisture from said inner fabric layer, and transporting said moisture upwardly away from the lower crotch area and outwardly away from the skin of the wearer, the width of said moisture transport insert tapering from the Upper crotch area towards the lower crotch area of the garment for providing greater surface area and moisture absorption capacity in the upper crotch area to promote transport of moisture upwardly from said lower crotch area to said upper crotch area to facilitate moisture dispersal; and
   (c) an outer fabric layer residing adjacent said intermediate fabric layer for receiving and dispersing moisture wicked outwardly from said inner and intermediate fabric layers, said outer fabric layer comprising the outer shell fabric of said panel.

2. A moisture-management garment according to claim 1, wherein said garment further comprises a top panel extending generally from a front waist portion of said garment to the upper crotch area of said garment and partially overlapping said moisture-management panel; said top panel and said moisture-management panel defining, in the area of said overlap, a laterally-extending fly opening formed there between.

3. A moisture-management garment according to claim 1, wherein said inner fabric layer is constructed of hydrophobic yarns.

4. A moisture-management garment according to claim 3, wherein said inner fabric layer includes fibers having a high surface area in relation to their volume.

5. A moisture-management garment according to claim 1, wherein said inner fabric layer is constructed of yarns chosen from the group consisting of polyester, polypropylene, and nylon fibers.

6. A moisture-management garment according to claim 1, wherein said moisture transport insert is constructed of hydrophobic yarns.

7. A moisture-management garment according to claim 1, wherein said moisture transport insert is constructed of yarns chosen from the fiber group consisting of rayon, polyester, cotton, and a blend of polyester and cotton.

8. A moisture-management garment according to claim 1, wherein said moisture transport insert is secured to at least one of said inner and outer fabric layers by sewn stitches.

9. A moisture-management garment according to claim 1, wherein said outer fabric layer is constructed of hydrophilic yarns.

10. A moisture-management garment according to claim 1, wherein said outer fabric layer is constructed of yarns chosen from the fiber group consisting of hydrophilic nylon, cotton, a blend of cotton and polyester, rayon, and a blend of hydrophilic nylon and conventional nylon.

11. A moisture-management garment according to claim 1 or 2, wherein said garment comprises a man's brief.

12. A moisture-management garment according to claim 1 or 2, wherein said garment comprises a man's boxer short or pajama bottom.

13. A moisture-management garment according to claim 1, wherein said garment comprises a woman's panty.

14. A moisture-management garment according to claim 1 or 9, wherein said garment comprises women's panty hose.

15. A moisture-management support garment including a moisture-management support pouch secured to and extending generally from a front waist area of the garment to a lower crotch area of the garment, said support pouch comprising:
   (a) an inner fabric layer including moisture wicking fibers for residing in skin contact during garment wear;
   (b) an intermediate fabric layer comprising one or more moisture transport inserts residing adjacent to said inner fabric layer, said one or more moisture transport inserts formed of one or more fabrics for receiving moisture from said inner fabric layer, and for transporting said moisture upwardly away from the lower crotch area and outwardly away from the skin of the wearer, said one or more moisture transport inserts comprising first and second longitudinally-extending wicking strips positioned in respective side sections of said moisture-management pouch and extending generally from the waist area of the garment to the lower crotch area of the garment; and
   (c) an outer fabric layer residing adjacent said intermediate fabric layer for receiving and dispersing moisture wicked outwardly from said inner and intermediate fabric layers, said outer fabric layer comprising the outer shell fabric of said support pouch.

16. A moisture-management support garment according to claim 15, wherein said inner fabric layer is constructed of hydrophobic yarns.

17. A moisture-management support garment according to claim 16, wherein said inner fabric layer includes fibers having a high surface area in relation to their volume.

18. A moisture-management support garment according to claim 15, wherein said inner fabric layer is constructed of yarns chosen from the fiber group consisting of polyester, polypropylene, and nylon fibers.

19. A moisture-management support garment according to claim 17 or 18, wherein said inner fabric layer includes elastic yarns for providing added stretch and support strength in the support pouch of the garment.

20. A moisture-management support garment according to claim 15, wherein said one or more moisture transport inserts are constructed of hydrophobic yarns.

21. A moisture-management support garment according to claim 15, wherein said one or more moisture transport inserts are constructed of yarns chosen from the fiber group consisting of rayon, polyester, cotton, and a blend of polyester and cotton.

22. A moisture-management support garment according to claim 20 or 21, wherein said one or more moisture transport inserts include elastic yarns for allowing said moisture transport inserts to stretch as said inner and outer fabric layers stretch.

23. A moisture-management support garment according to claim 15, wherein said one or more moisture transport inserts are secured to at least one of said inner and outer fabric layers.

24. A moisture-management support garment according to claim 15, wherein said outer fabric layer is constructed of hydrophobic yarns.

25. A moisture-management support garment according to claim 15, wherein said outer fabric layer is constructed of hydrophilic yarns.

26. A moisture-management support garment according to claim 15, wherein said outer fabric layer is constructed of a blend of hydrophilic and hydrophobic yarns.

27. A moisture-management support garment according to claim 15, wherein said outer fabric layer is constructed of yarns chosen from the fiber group consisting of hydrophilic nylon, cotton, a blend of cotton and polyester, rayon, and a blend of hydrophilic nylon and conventional nylon.

28. A moisture-management support garment according to claim 24, 25, 26, or 27, wherein said outer fabric layer includes elastic yarns for proving added stretch and support strength in the support pouch of the garment.

29. A moisture-management support garment according to claim 15, wherein said support garment further comprises a relatively wide waistband for holding said support garment and said moisture-management pouch close to the body of the wearer.

30. A moisture-management support garment according to claim 29, wherein said waistband is constructed of elastic yarns and yarns chosen from the fiber group consisting of conventional nylon, cotton, rayon, and blends of hydrophilic nylon and conventional nylon.

31. A moisture-management support garment according to claim 30, wherein said support garment comprises a man's brief.

* * * * *